US010883828B2

(12) United States Patent
Zhu et al.

(10) Patent No.: US 10,883,828 B2
(45) Date of Patent: Jan. 5, 2021

(54) CAPSULE ENDOSCOPE

(71) Applicant: STMicroelectronics (Beijing) R&D Co. Ltd., Beijing (CN)

(72) Inventors: Peng Fei Zhu, Beijing (CN); Yong Qiang Wu, Beijing (CN); Kai Feng Wang, Beijing (CN); Hong Xia Sun, Beijing (CN)

(73) Assignee: STMICROELECTRONICS (BEIJING) R&D CO., LTD, Beijing (CN)

( * ) Notice: Subject to any disclaimer, the term of this patent is extended or adjusted under 35 U.S.C. 154(b) by 180 days.

(21) Appl. No.: 15/645,371

(22) Filed: Jul. 10, 2017

(65) Prior Publication Data

US 2017/0307373 A1    Oct. 26, 2017

Related U.S. Application Data

(63) Continuation of application No. 13/329,293, filed on Dec. 18, 2011, now abandoned.

(30) Foreign Application Priority Data

Dec. 17, 2010  (CN) .......................... 2010 1 0603106

(51) Int. Cl.
*G01C 19/02* (2006.01)
*A61B 1/00* (2006.01)
(Continued)

(52) U.S. Cl.
CPC ............ *G01C 19/02* (2013.01); *A61B 1/0002* (2013.01); *A61B 1/00016* (2013.01);
(Continued)

(58) Field of Classification Search
CPC ..... G01C 19/02; A61B 1/041; A61B 1/00016; A61B 1/0002; A61B 1/00032; A61B 1/00057
See application file for complete search history.

(56) References Cited

U.S. PATENT DOCUMENTS

| 4,159,690 A * | 7/1979 | Farris ................... G05D 1/0875 114/275 |
| 5,253,647 A | 10/1993 | Takahashi et al. |

(Continued)

FOREIGN PATENT DOCUMENTS

| CN | 2735933 Y | 10/2005 |
| CN | 1868396 A | 11/2006 |

(Continued)

OTHER PUBLICATIONS

L3G4200D, "MEMS Motion Sensor: Three-Axis Digital Outpost Gyroscope," Feb. 2010, Doc ID 17116 Rev. 1, www.st.com, 24 pages.

(Continued)

*Primary Examiner* — Timothy J Neal
*Assistant Examiner* — Jae Woo
(74) *Attorney, Agent, or Firm* — Slater Matsil, LLP

(57) ABSTRACT

An embodiment comprises and apparatus having an image capture device with an image axis and a gyroscope operable to indicate the orientation of the image axis. An embodiment of a capsule endoscopy system comprises an imaging capsule and an external unit. The imaging capsule may comprise an image capture device having an image axis and a gyroscope operable to indicate the orientation of the image axis. The external unit may comprise a gyroscope operable to indicate an orientation of a subject and a harness wearable by a subject and operable to align the gyroscope with the subject. The imaging capsule may send and image to an external unit for processing and display, and the external unit (Continued)

may provide for calculation of the image-axis orientation relative to the body.

26 Claims, 5 Drawing Sheets

(51) Int. Cl.
   *A61B 1/04* (2006.01)
   *G01C 19/00* (2013.01)
   *A61B 1/06* (2006.01)
(52) U.S. Cl.
   CPC ...... *A61B 1/00032* (2013.01); *A61B 1/00057* (2013.01); *A61B 1/00158* (2013.01); *A61B 1/041* (2013.01); *A61B 1/0661* (2013.01); *G01C 19/00* (2013.01)

(56) References Cited

U.S. PATENT DOCUMENTS

| | | | |
|---|---|---|---|
| 5,749,540 A * | 5/1998 | Arlton | B64C 27/82 244/17.13 |
| 5,776,050 A | 7/1998 | Chen et al. | |
| 5,821,414 A * | 10/1998 | Noy | E21B 47/022 73/152.54 |
| 6,432,041 B1 | 8/2002 | Taniguchi et al. | |
| 6,442,417 B1 | 8/2002 | Shahidi et al. | |
| 6,690,963 B2 | 2/2004 | Ben-Haim et al. | |
| 6,895,305 B2 * | 5/2005 | Lathan | A63F 13/00 700/245 |
| 7,211,042 B2 | 5/2007 | Chatenever et al. | |
| 7,585,273 B2 | 9/2009 | Adler et al. | |
| 7,603,160 B2 | 10/2009 | Suzuki et al. | |
| 7,993,265 B2 | 8/2011 | Suzushima et al. | |
| 8,050,738 B2 | 11/2011 | Minai et al. | |
| 8,214,017 B2 * | 7/2012 | Sato | A61B 1/0005 345/158 |
| 2001/0002121 A1 * | 5/2001 | Seto | H02J 7/1423 340/661 |
| 2002/0099310 A1 | 7/2002 | Kimchy et al. | |
| 2002/0160746 A1 * | 10/2002 | Yoshioka | G08B 29/181 455/404.1 |
| 2003/0028078 A1 * | 2/2003 | Glukhovsky | A61B 1/041 600/109 |
| 2003/0137433 A1 * | 7/2003 | Schiller | G01C 19/5719 340/973 |
| 2003/0199756 A1 | 10/2003 | Kawashima | |
| 2003/0216639 A1 | 11/2003 | Gilboa et al. | |
| 2004/0199054 A1 | 10/2004 | Wakefield | |
| 2005/0027178 A1 * | 2/2005 | Iddan | A61B 1/041 600/339 |
| 2005/0043587 A1 | 2/2005 | Fujimori et al. | |
| 2005/0143643 A1 * | 6/2005 | Mimai | A61B 1/00016 600/407 |
| 2005/0187479 A1 * | 8/2005 | Graumann | A61B 1/00147 600/476 |
| 2005/0228230 A1 | 10/2005 | Schara et al. | |
| 2007/0003612 A1 | 1/2007 | Williams | |
| 2008/0021282 A1 | 1/2008 | Hoeg et al. | |
| 2008/0039688 A1 | 2/2008 | Minai et al. | |
| 2008/0300453 A1 * | 12/2008 | Aoki | A61B 1/00156 600/103 |
| 2009/0147993 A1 * | 6/2009 | Hoffmann | G02B 27/0093 382/103 |
| 2009/0227840 A1 | 9/2009 | Uchiyama et al. | |
| 2009/0227864 A1 * | 9/2009 | Sato | A61B 1/0005 600/424 |
| 2010/0010300 A1 | 1/2010 | Gilad | |
| 2010/0039381 A1 * | 2/2010 | Cretella, Jr. | G06F 3/0317 345/158 |
| 2010/0169409 A1 * | 7/2010 | Fallon | G06F 19/3418 709/203 |
| 2011/0144573 A1 * | 6/2011 | Rofougaran | A61B 5/6805 604/66 |
| 2012/0157769 A1 | 6/2012 | Zhu et al. | |
| 2012/0172681 A1 | 7/2012 | Sun et al. | |

FOREIGN PATENT DOCUMENTS

| | | |
|---|---|---|
| CN | 101351145 A | 1/2009 |
| CN | 101502412 A | 8/2009 |
| JP | 2006263167 A | 10/2006 |
| WO | 9605768 A1 | 2/1996 |

OTHER PUBLICATIONS

L3G4200DH, "MEMS Motion Sensor: Three-Axis Digital Outpost Gyroscope," Apr. 2010, Doc ID 17300 Rev 1, www.st.com, 28 pages.

* cited by examiner

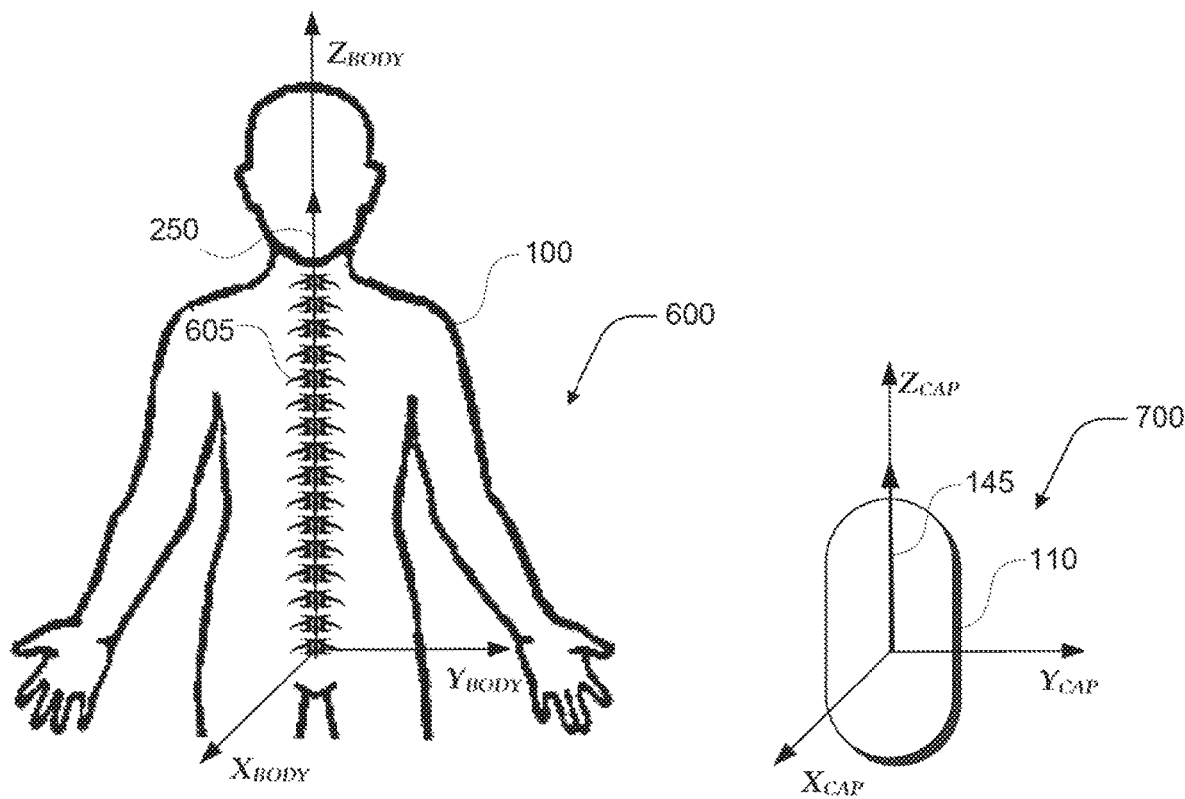
Fig.6
Fig.7
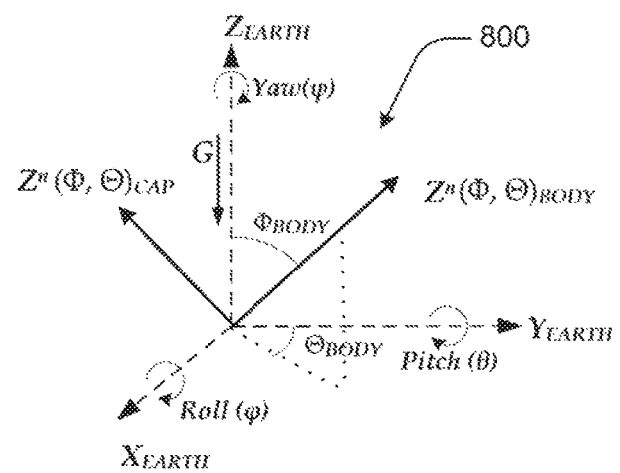
Fig.8

CAPSULE ENDOSCOPE

CROSS-REFERENCE TO RELATED APPLICATIONS

This application is a continuation of U.S. patent application Ser. No. 13/329,293, filed on Dec. 18, 2011, which claims priority to Chinese Patent Application No. 201010603106.2, filed on Dec. 17, 2010, which applications are hereby incorporated herein by reference.

SUMMARY

An embodiment of an image capture device comprises an image axis and a gyroscope operable to indicate the orientation of the image axis An embodiment of a capsule endoscopy system comprises an imaging capsule and an external unit. The imaging capsule may include an image capture device having an image axis and a gyroscope operable to indicate the orientation of the image axis. The external unit may include a gyroscope operable to indicate an orientation of a subject and a harness wearable by the subject, and is operable to align the gyroscope with an axis of the subject. The imaging capsule may send an image to the external unit for processing and display, and the external unit may calculate the image-axis orientation relative to the body.

For example, in such an embodiment, the imaging capsule may be ingested and images of a subject's gastrointestinal system, and the external unit may determine the orientation of the imaging capsule's image axis relative to the subject's body.

BRIEF DESCRIPTION OF THE DRAWINGS

The present disclosure is presented by way of at least one non-limiting exemplary embodiment, illustrated in the accompanying drawings in which like references denote similar elements, and in which:

FIG. 6 is diagram of the human subject of FIGS. 1-3 and of a coordinate system for the subject's frame of reference.

FIG. 7 is a diagram of the imaging capsule of FIGS. 1 and 4 and of coordinate system for the capsule's frame of reference.

FIG. 8 is a diagram of a coordinate system for a frame of reference within which the human subject of FIG. 6 and the imaging capsule of FIG. 7 may be located.

DETAILED DESCRIPTION OF ILLUSTRATIVE EMBODIMENTS

Endoscopy, or internal examination of a living subject such as a human, may be performed with an endoscope that is inserted into a body opening (e.g., mouth or anus) and that allows a physician to internally view a body cavity (e.g., esophagus, stomach, colon, or intestine) that is accessible via the opening. Examination of the gastrointestinal tract ("GI tract"), for example, includes inserting the endoscope into the mouth, down the esophagus, and into the stomach and/or intestines. Similarly, examination of the colon (e.g., a colonoscopy), for example, includes inserting the endoscope through the anus into the colon.

Unfortunately, such a procedure may be invasive and uncomfortable for a subject, and may necessitate general anesthesia. Moreover, such a procedure may require sterile endoscopy equipment and a sterile environment. Accordingly, an endoscopy procedure is generally performed in a hospital setting, which may increase the cost of such a procedure.

Figure 1:
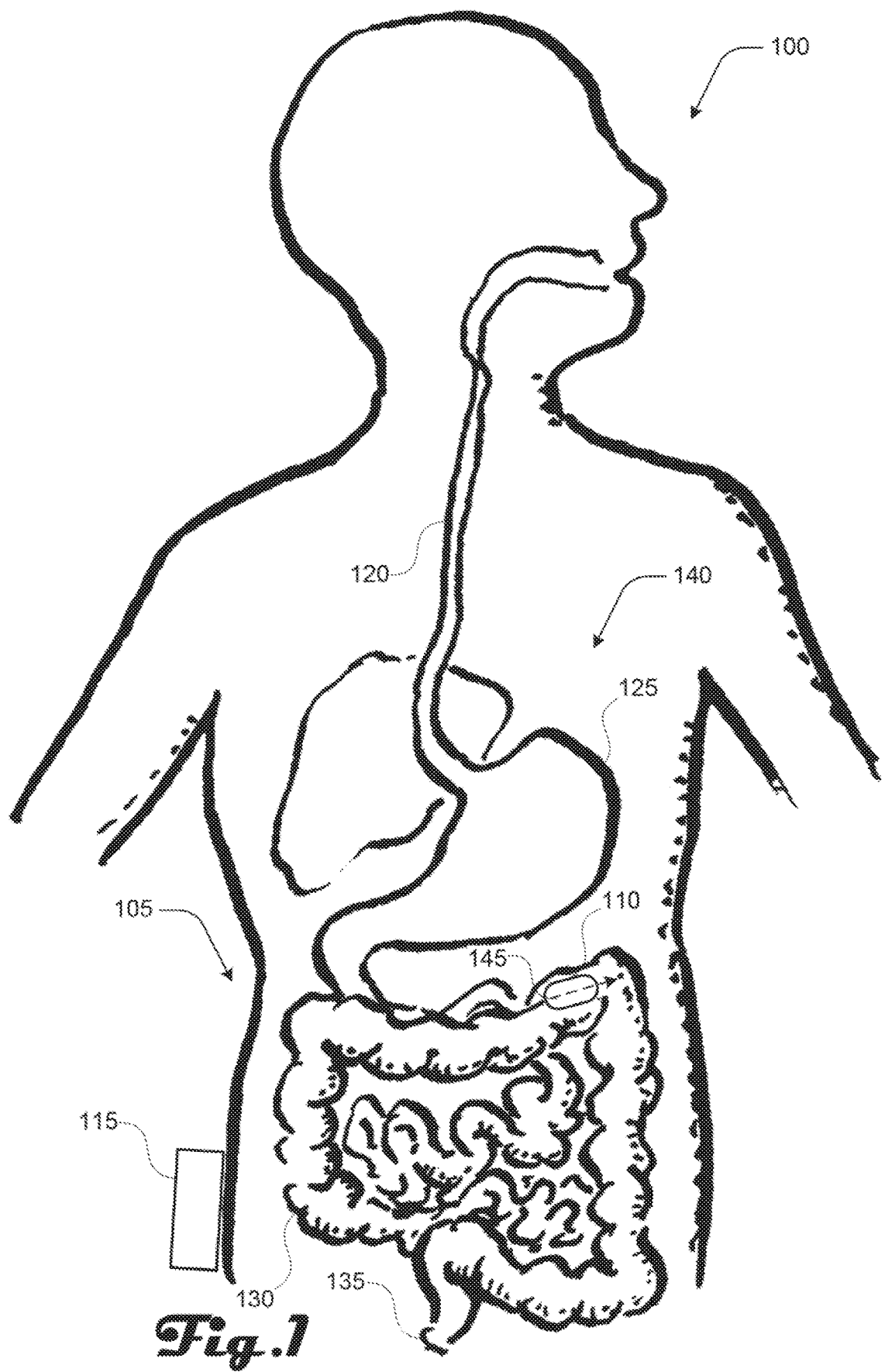
FIG. 1 is a cross-sectional view of a human subject and of an embodiment of a capsule endoscopy system that includes an imaging capsule and an external unit.

FIG. 1 is a cross-sectional view of a human subject 100 and an embodiment of a capsule endoscopy system 105 that includes an imaging capsule 110 and an external unit 115. As discussed in further detail herein, the imaging capsule 110 may be swallowed, and thereafter may pass through the esophagus 120, through the stomach 125, through the intestines 130 (the esophagus, stomach, and intestines may be collectively referred to as the GI tract 140), and out the anus 135 as depicted in FIG. 1. As it makes its journey through the subject's GI tract 140, the imaging capsule 110 may be operable to capture images of the GI tract 140 along an imaging axis 145 and to transmit the captured images to the external unit 115. The imaging capsule 110 may be recovered when it leaves the body of the subject 100, or may be disposed as part of the subject's waste (e.g., via a toilet during a bowel movement).

Compared to conventional endoscopy as discussed above, the endoscopy system 105 described herein is non-invasive because a subject 100 need only swallow the imaging capsule 110 and wear the external unit 115 as the imaging capsule travels through his/her GI tract 140. Therefore, no anesthesia is believed to be required in most cases, and imaging via the endoscopy system 105 need not be performed in a sterile hospital setting, or even at a doctor's office. In fact, once the subject 100 swallows the imaging capsule 110, the subject may move about normally as the imaging capsule captures images of the subject's GI tract 140. This may significantly reduce the cost of endoscopy procedures and may significantly reduce the discomfort and inconvenience of the subject 100.

The imaging capsule 110 may assume numerous orientations relative to the subject 100 while traveling through the GI tract 140, such that the image axis 145 may be pointing in any direction at any given time. Therefore, images captured by the imaging capsule 110 may be taken from numerous orientations within the GI tract. As described further herein, because a physician may want to know the relative orientation of each image relative to the GI tract 140 for purposes of analysis and diagnosis, the external unit 115 and imaging capsule 110 may be operable to indicate, for each image, the orientation of the imaging capsule 110 relative to a frame of reference of the subject 100. For example, for images of the subject's stomach, a doctor may wish to know if the image is of, e.g., the back of the stomach, the front of the stomach, the top of the stomach, or the bottom of the stomach.

Figure 2:
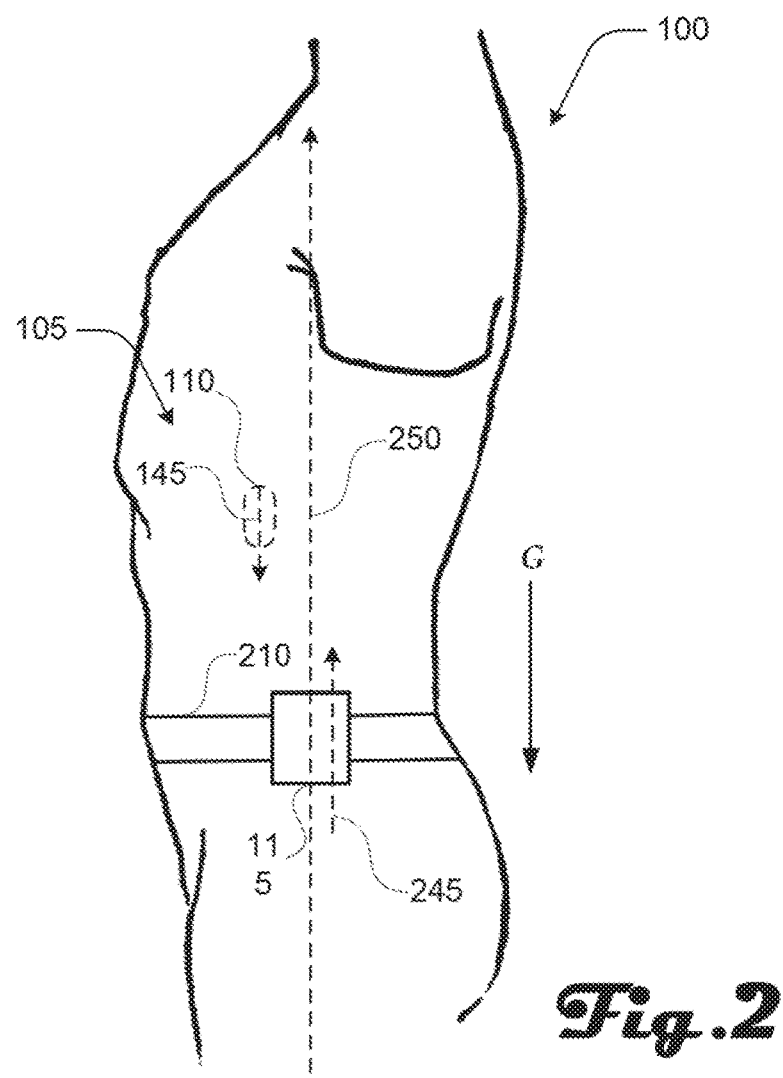
FIGS. 2 and 3 are side views of the human subject of FIG. 1 in standing and supine positions, respectively.
Figure 3:
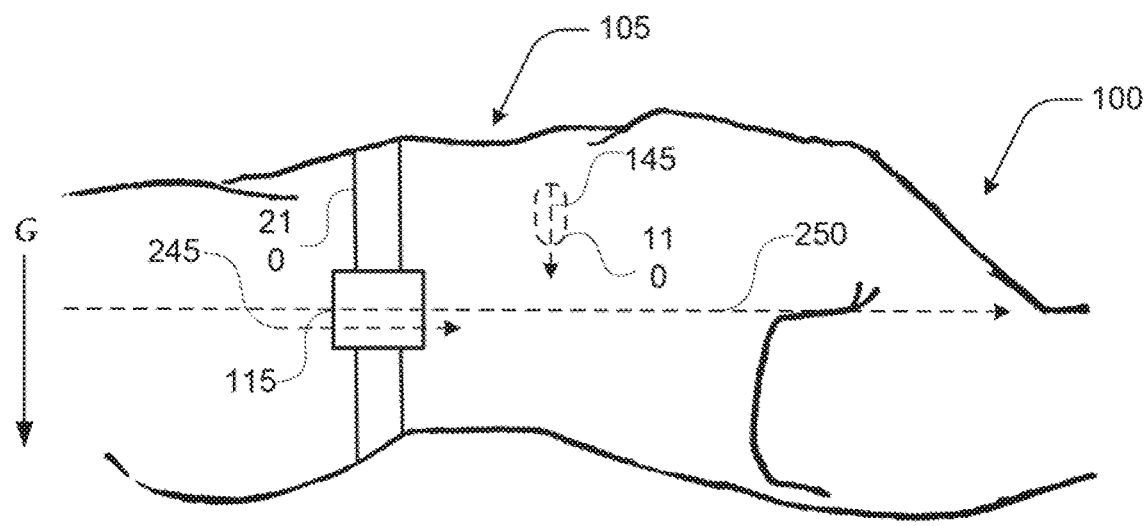

FIGS. 2 and 3 are side views of the human subject 100 respectively standing and lying down, with an embodiment of the imaging capsule 110 inside the subject 100 and an embodiment of an external unit 115 being worn by the subject 100.

The external unit 115 is coupled to the subject 100 with a harness 210, which may be a belt or strap of a suitable material that encircles the subject 100 and maintains an axis 245 of the frame of reference of the external unit 115 in alignment with an axis 250 of the subject's frame of reference regardless of how the subject 100 may move. That is, the harness 210 maintains the unit's axis 245 approximately parallel to or approximately co-linear with the subject axis 250. For example, the subject 100 in FIG. 2 is shown standing with the body axis 250 aligned with a gravity vector $\vec{G}$ and the subject in FIG. 3 is laying down with the body axis 250 perpendicular to the gravity vector $\vec{G}$. In both subject orientations, the harness 210 maintains the external-unit axis 245 in approximate alignment with the body axis 250.

Additionally, FIGS. 2 and 3 depict the imaging capsule 110 in two different orientations relative to the frame of reference of the subject 100. Although both FIGS. 2 and 3 depict the image axis 145 of the capsule 110 oriented in the same direction relative to the earth's frame of reference, i.e., aligned with the gravity vector $\vec{G}$, the orientation of the image axis relative to the frame of reference of the subject 100, and thus relative to the body axis 250, is different. FIG. 2 depicts the image axis 145 pointing toward the distal inferior extremities of the subject 100 (e.g. down toward the legs, etc.) in parallel with the body axis 250. However, FIG. 3 depicts the image axis 145 pointing toward the posterior of the subject 100, perpendicular to the body axis 250. As discussed herein, the orientation of the image axis 145 relative to the body axis 250, and thus to the subject's frame of reference, 100 may be determined based on orientation indications provided by the imaging capsule 110 and the external unit 115. The orientation of images captured by the imaging capsule 110 may thereby be determined relative to the body axis 250 as further discussed herein so that a physician, such as a radiologist, may determine the orientation of each image relative to the subject's GI tract. That is, an image's orientation may be toward the front of the subject, toward the back of the subject, etc. Knowing an image's orientation relative to the subject may facilitate the physician's analysis of the image, and may facilitate the physician formulating a diagnosis of the subject.

Figure 4:
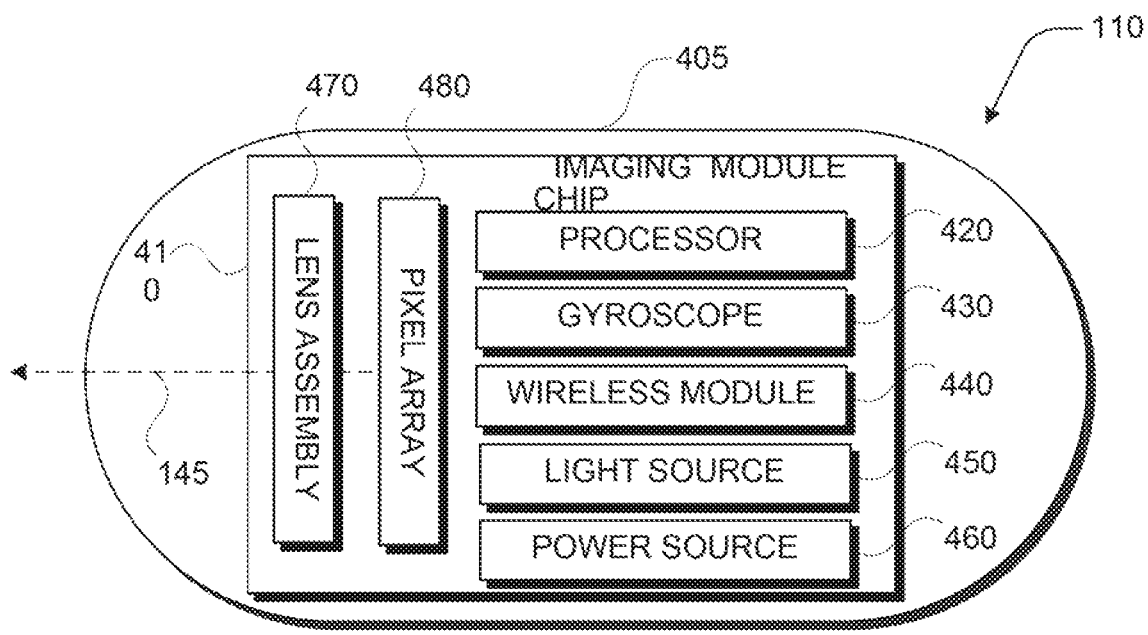
FIG. 4 is a block diagram of an embodiment of the imaging capsule of FIG. 1.

FIG. 4 is a block diagram of an embodiment of the imaging capsule 110 of FIGS. 1-3. The imaging capsule 110 includes a housing or capsule shell 405, and disposed within the housing is an imaging-module integrated circuit (IC) 410, which may be formed from one or more integrated-circuit dies. For example, the imaging-module IC 410 may be a system on a chip.

The imaging module chip 410 includes a processor 420, a gyroscope 430, a wireless transceiver module 440, a light source 450, a power source 460, a lens assembly 470, and a pixel array 480. The focal axis of the lens assembly 470 and the array axis normal to the center of the pixel array 480 are approximately aligned along the image axis 145. That is, the pixel array 480 is operable to capture an image of an object toward which the image axis 145 points.

The shell 405 may be formed of any suitable material, and may be any suitable size and shape. For example, in an embodiment, the shell 405 may be operable to be ingested and to pass through the gastrointestinal tract of the subject 100 (FIGS. 1-3). Therefore, the shell 405 may be of a size (e.g., pill or medicinal-capsule size) suitable for ingestion by the subject 100, and may be formed from a material that is resilient to the conditions experienced within the gastrointestinal tract of the subject such that the imaging capsule may remain functional for its entire journey through the subject's GI tract 140. Additionally, at least the portion of the shell 405 through which the image axis 145 extends may be transparent so that images may be captured through the shell. For example, if the pixel array 480 is sensitive to electromagnetic energy having wavelengths in the visible portion of the electromagnetic spectrum, then this portion of the shell 405 may be transparent to these visible wavelengths. Likewise, if the pixel array 480 is sensitive to electromagnetic energy having wavelengths in the infrared portion of the electromagnetic spectrum, then this portion of the shell 405 may be transparent to these infrared wavelengths. Additionally, the shell 405 and other components of the imaging capsule 110 may be made of environmentally friendly material so that if the imaging capsule is intended to be disposable (i.e., not recovered when leaving the subject 100), the imaging capsule would have little or no negative environmental impact as waste.

The imaging-module IC 410 may be an integrated circuit, a hybrid integrated circuit, a micro-electro-mechanical system (MEMS), or any suitable system. Furthermore, as discussed above, the components of the imaging-module IC 410 may be disposed on a single IC die or on multiple IC dies. Additionally, the imaging-module IC 410 may include more or fewer components than are described herein, and such components may be configured in any suitable arrangement.

The processor 420 may be any suitable processor, processing system, controller, or module, and may be programmable to control one or more of the other components of the imaging capsule 110. Furthermore, the processor 420 may perform image processing on images captured by the pixel array 480 before the images are transmitted to the external unit 115 (FIG. 1-3).

The gyroscope 430 may be any suitable device operable to indicate a degree of rotation about one or more coordinate axes of the gyroscope's frame of reference. For example, the gyroscope 430 may be operable to detect "yaw", "pitch", and "roll" (i.e., rotation) about coordinate X, Y, and Z axes, respectively. Examples of gyroscopes suitable for the gyroscope 430 include the STMicroelectronics L3G4200DH and the L3G4200D. In an embodiment, there may be a plurality of gyroscopes 430.

The wireless module 440 may be any suitable device that is operable to send and receive wireless communications. For example, the wireless module 440 may be operable to send to the external unit 115 (FIGS. 1-3 & 5) images captured by the pixel array 480 and indications of rotation from the gyroscope 430; the external unit may use these indications of rotation to calculate the orientation of the image axis 145 for each received image. Furthermore, the wireless module 440 may allow one to control the operation of one or more components of the imaging capsule 110, and may allow one to program the processor 420. Moreover, the wireless module 440 may send status information to the external unit 115, such as the level of power remaining in the power source 460, or the intensity of the illumination provided by the light source 450 (the imaging capsule 110 may include a sensor, not shown in FIG. 4, to measure the intensity of the light source).

The light source 450 may be any suitable device (e.g., one or more light-emitting diodes) operable to provide illumination to aid in capturing images. For example, the light source may be operable to provide sufficient illumination while in the gastrointestinal tract of the subject 100 such that the pixel array 480 may capture an image. The light source 450 may provide continuous illumination, or may provide flash illumination as is suitable for the application, for example, under the control of the processor 420. Additionally, the intensity of illumination may be modified, e.g., by the processor 420 (the light source 450, or the image capsule 110, may include an intensity sensor (not shown in FIG. 4) that is coupled to the processor). Alternatively, the light source 450 may be omitted, for example, if the pixel array 480 is sensitive to infrared wavelengths. In an embodiment, there may be a plurality of light sources 450.

The power source 460 may be any suitable source of power such as a battery, and may provide power to one or more components of the imaging capsule 110. The power source 460 may be recharged via a wired technique, or may be recharged wirelessly (e.g., via RF energy). In an embodiment, there may be a plurality of power sources 460.

The lens assembly 470 may be operable to focus, or otherwise to modify electromagnetic energy (e.g., visible light) such that the energy may be sensed by the pixel array 480 to capture an image. Collectively, the lens assembly 470 and pixel array 480 may constitute an image-capture apparatus, and may be arranged as a single imaging module, assembly, or unit. As discussed above, the normal to the center of the pixel array 480 and the focal axis of the lens assembly 470 are approximately aligned along the image axis 145, which "points" in the direction of an object (or portion of an object) whose image the pixel array may capture. The lens assembly 470 may be any suitable type of imaging lens assembly, such as a macro lens, process lens, fisheye lens, or stereoscopic lens.

In an embodiment, the pixel array 480 and lens assembly 470 may be operable to capture images in various regions of the electromagnetic spectrum, including infrared, ultraviolet, or within visible light. In an embodiment, the pixel array 480, lens assembly 470, or both the pixel array and the lens assembly, may be separate from the imaging module chip 410. Additionally, in an embodiment, the lens assembly 470 may be omitted. In an embodiment, there may be a plurality of pixel arrays 480 lens assemblies 470.

Figure 5:
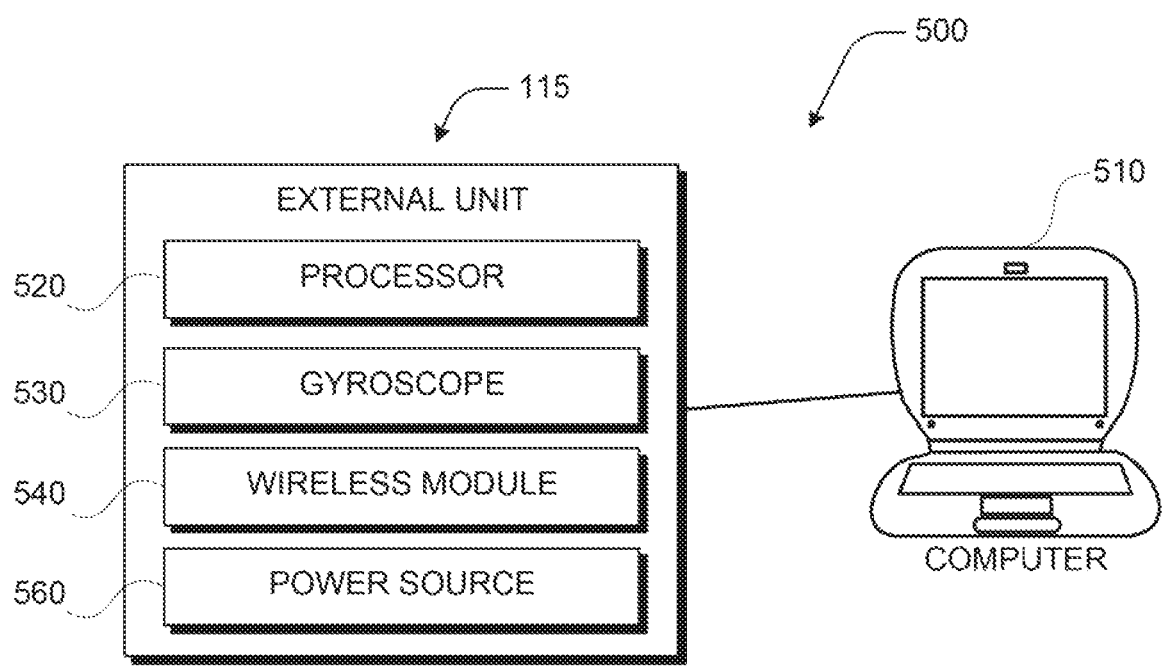
FIG. 5 is a block diagram of an embodiment of the external unit of FIG. 1 operatively connected with a computer.

FIG. 5 is a block diagram of an embodiment of an external system 500, which includes an embodiment of the external unit 115 and an embodiment of an optional computer 510 coupled to the external unit. The external unit 115 includes a processor 520, a gyroscope 530, a wireless module 540, and a power source 560.

The processor 520 may be any suitable processor, processing system, controller, or module, and may be programmable to control one or more of the other components of the imaging capsule 110. Furthermore, the processor 520 may perform image processing on images captured by the pixel array 480.

The gyroscope 530 may be any suitable device operable to indicate a degree of rotation about one or more coordinate axes of the gyroscope's frame of reference. For example, the gyroscope 530 may be operable to detect "yaw", "pitch", and "roll" (i.e., rotation) about coordinate X, Y, and Z axes, respectively.

The wireless module 540 may be operable to send and receive wireless communications. For example, the wireless module 540 may be operable to receive from the imaging capsule 110 (FIGS. 1-4) images captured by the pixel array 480 and indications of rotation from the gyroscope 430. The wireless module 540 may also be operable to wirelessly communicate with the computer 510. The wireless module 540 may be any suitable device that is operable to send and receive wireless communications. Furthermore, the wireless module 540 may allow one to control the operation of one or more components of the external unit 115, and may allow one to program the processor 520 via, e.g., the computer 510. Moreover, the wireless module 540 may send status information to the computer 510, such as the level of power remaining in the power source 560. Furthermore, the wireless module 540 may act as a "go-between" for the capsule 110 (FIG. 4) and another device such as the computer 510.

The computer 510 may be any suitable computing device (e.g., a laptop or desktop computer) that is directly or wirelessly coupled with the external unit 115, and may be operable to program the external unit 115, obtain stored data from the external unit 115, process data obtained from the external unit 115, and the like. The computer 510 may also be operable to program the processor 420 of the imaging capsule 110 (FIG. 4) either directly or via the external unit 115. Furthermore, the computer 510 may be operable to process image data received from the imaging capsule 110 directly or via the external unit 115, and to recover one or more images from this data, to determine the orientation of the image axis 145 (FIG. 4) for each recovered image as discussed below in conjunction with FIGS. 6-8, and to display each recovered image. The computer 510 may also be able to send the recovered images and other related information to a remote location, such as a doctors' office, via the internet. Accordingly, the subject 100 (FIGS. 1-3 and 6) may be able to go about his/her normal activities such as working or sleeping as the imaging capsule 110 travels through the subject's GI tract 130 (FIG. 1), and images captured by the imaging capsule could be sent in real time to the doctor's office over the Internet. The power source 560 may be any suitable source of power such as a battery, and may provide power to one or more components of the external unit 115. The power source 560 may be recharged via conventional wired methods, or may be recharged wirelessly (e.g., via RF energy). In an embodiment, there may be a plurality of power sources 560.

In an embodiment, the endoscopy system 105 described herein may also be used to capture images within a non-human subject 100. Additionally, the endoscopy system 105 or components thereof may be used to capture images within non-living systems, such as systems of pipes, a moving body of water, or the like.

FIG. 6 is a coordinate system 600 of a frame of reference of the subject 100, the coordinate system having the axes $X_{BODY}$, $Y_{BODY}$, and $Z_{BODY}$, interposed on the subject, wherein the $Z_{BODY}$ axis is aligned with the body axis 250 of the subject. Given that the spine 605 of the subject 100 is not typically linear within the coronal plane of the subject, the $Z_{BODY}$ and the body axis 250 may be aligned with a hypothetically straightened spine, or may only be aligned with the spine along the sagittal plane. As the subject 100 changes position the $X_{BODY}$, $Y_{BODY}$, and $Z_{BODY}$ remain stationary relative to the subject. In other words, the $X_{BODY}$, $Y_{BODY}$, and $Z_{BODY}$ are fixed relative to the subject's 100 frame of reference. For example, if the subject 100 lies down, then the $Z_{BODY}$ axis will maintain the same alignment with the body axis 250.

As depicted in FIG. 6, the $X_{BODY}$ axis extends along the mid-sagittal plane of the subject 100 perpendicular to the frontal plane of the subject, and the $Y_{BODY}$ axis is perpendicular to the mid-sagittal plane of the subject or co-linear with and along the frontal plane of the subject. The $Z_{BODY}$ axis extends in alignment with the body axis (i.e., parallel to the body axis 250 superiorly from the axis origin).

In an embodiment, the external unit axis 245 (FIGS. 2 and 3) (i.e., the orientation of the external unit 115) is assumed to represent the body frame of reference 600. Because external unit 115 may be worn on the outside of the subject 100, the body frame of reference 600 and the external unit axis 245 may not be directly aligned. Therefore, an assumption may be made that the external unit axis 245 is aligned with the body axis 250, and that the external unit 115 frame of reference is the same as the subject 100 frame of reference 600. Accordingly, the external unit 115 worn by the subject 100 may be assumed to be detecting changes in the orientation of the body axis 250 within the subject frame of reference.

Although the $X_{BODY}$, $Y_{BODY}$, and $Z_{BODY}$ are depicted as having specific orientations relative to the body of the subject 100, in another embodiment, the $X_{BODY}$, $Y_{BODY}$, and $Z_{BODY}$ axes may have different orientations relative to the subject, and need not be aligned with a plane, the spine 605, or other part of the body. Therefore, the alignments of the $X_{BODY}$, $Y_{BODY}$, and $Z_{BODY}$ axes shown in FIG. 6 merely represent one possible configuration of the axes. Additionally, the $X_{BODY} Y_{BODY}$ plane may be moved up and down relative to the $Z_{BODY}$ axis.

FIG. 7 is a coordinate system 700 frame of reference for the capsule 110 having the axes $X_{CAP}$, $Y_{CAP}$, and $Z_{CAP}$, interposed on the imaging capsule, wherein the $Z_{CAP}$ axis is aligned (i.e., parallel to or co-linear) with the image axis 145 of the imaging capsule. As the imaging capsule 110 changes position, the $X_{BODY}$, $Y_{BODY}$, and $Z_{BODY}$ axes remain stationary relative to the imaging capsule. In other words, the $X_{CAP}$, $Y_{CAP}$, and $Z_{CAP}$ are fixed relative to the imaging capsule's frame of reference. Additionally, as discussed above in conjunction with FIG. 6, the alignment of $X_{CAP}$, $Y_{CAP}$, and $Z_{CAP}$ may be in any desired orientation; for example, the $Z_{CAP}$ axis need not be aligned with the imaging axis 145, although such alignment may make easier the calculations for determining the orientation of the imaging axis 145 relative to the subject's frame of reference 600.

FIG. 8 is a terrestrial coordinate system 800 having the axes $X_{EARTH}$, $Y_{EARTH}$, and $Z_{EARTH}$, wherein the $Z_{EARTH}$ axis is aligned with vector $\vec{G}$, which represents the direction of the gravitational force of the earth. Depicted within the coordinate system 800 are a body orientation $Z^N_{BODY}$, and a cap orientation $Z^N_{CAP}$. The terrestrial coordinate system 800 is fixed to the earth's frame of reference. Additionally, the body orientation $Z^N_{BODY}$, and the cap orientation $Z^N_{CAP}$ respectively represent the orientation of the subject's 100 frame of reference and the imaging capsule's 110 frame of reference at a given time N relative to the origin of terrestrial coordinate system 800.

The $Z^N_{BODY}$ orientation represents an orientation of the $Z_{BODY}$ axis (FIG. 6) relative to the terrestrial coordinate system 800 at a given time N, e.g., $Z^1_{BODY}$, $Z^2_{BODY}$, $Z^3_{BODY}$, etc. For example, as the subject 100 changes position (e.g., lies down, bends over, reclines, etc.) the orientation of the $Z_{BODY}$ axis of the subject 100 would change relative to the terrestrial coordinate system 800.

The $Z^N_{CAP}$ orientation represents an orientation of the $Z^N_{CAP}$ axis (FIG. 7) relative to the terrestrial coordinate system 800 at a given time N (e.g., $Z^1_{CAP}$, $Z^2_{CAP}$, $Z^3_{CAP}$, etc.). For example, as the imaging capsule 110 changes orientation within the GI tract 140 of the subject 100 (as the image capsule moves through the gastrointestinal tract) the orientation of the $Z_{CAP}$ axis may change relative to the terrestrial coordinate system 800. Additionally, the orientation of the $Z_{CAP}$ axis may change relative to the $Z_{BODY}$ axis, and vice versa.

$Z^N_{CAP}$ and $Z^N_{BODY}$ may be defined within the terrestrial coordinate system 800 by spherical coordinates relative to the earth $X_{EARTH}$ $Y_{EARTH}$ $Z_{EARTH}$ coordinate system 800. For example, $\theta_{BODY}$ and $\phi_{BODY}$, are depicted in FIG. 8 as spherical coordinates of $Z^N_{BODY}$, where $\theta_{BODY}$ represents an angle from the positive $Y_{EARTH}$ axis projected in the $X_{EARTH}$ $Y_{EARTH}$ plane (e.g., in radians from 0 to $2\pi$) with the vertex being the origin, and where $\phi_{BODY}$ represents an angle from the positive $Z_{BODY}$ axis (e.g., in radians from 0 to $\pi$) with the vertex being the origin. Accordingly, $\theta_{BODY}$ and $\phi_{BODY}$, for example, define the orientation $Z^N_{BODY}$ from the origin of the $X_{EARTH}$ $Y_{EARTH}$ $Z_{EARTH}$ coordinate system 800. Similarly, $\theta_{CAP}$ and $\phi_{CAP}$ (not shown in FIG. 8), define the orientation $Z^N_{CAP}$ from the origin of $X_{EARTH}$ $Y_{EARTH}$ $Z_{EARTH}$ coordinate system 800.

As $Z^N_{CAP}$ changes direction relative to the terrestrial coordinate system 800 as the imaging capsule 110 moves through the gastrointestinal tract capturing images, knowing the orientation of $Z^N_{CAP}$ relative to $Z^N_{BODY}$ may be important when interpreting the images captured by the image capsule 110. For example, for a given image or a series of images, it may be important to determine whether the image axis 145 is pointing toward the back, legs, head, or front of the subject 100 so that the images may be properly interpreted or so that images may be combined.

Figure 9:
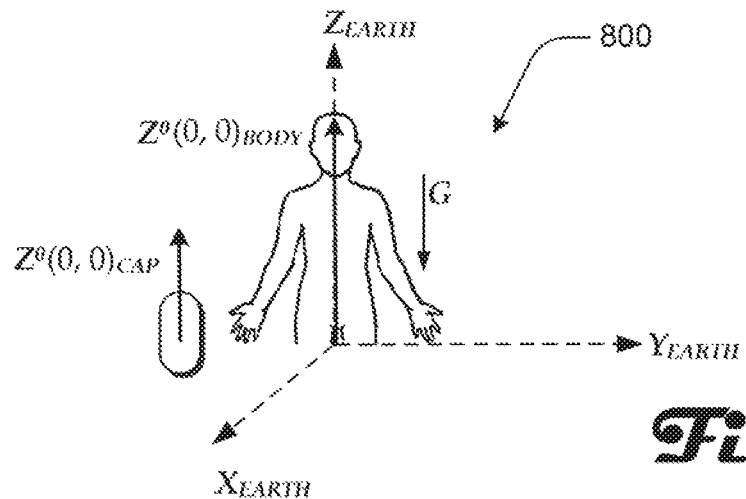
FIGS. 9-11 are diagram of additional coordinate systems for a frame of reference within which the human subject of FIG. 6 and the imaging capsule of FIG. 7 may be located.
Figure 10:
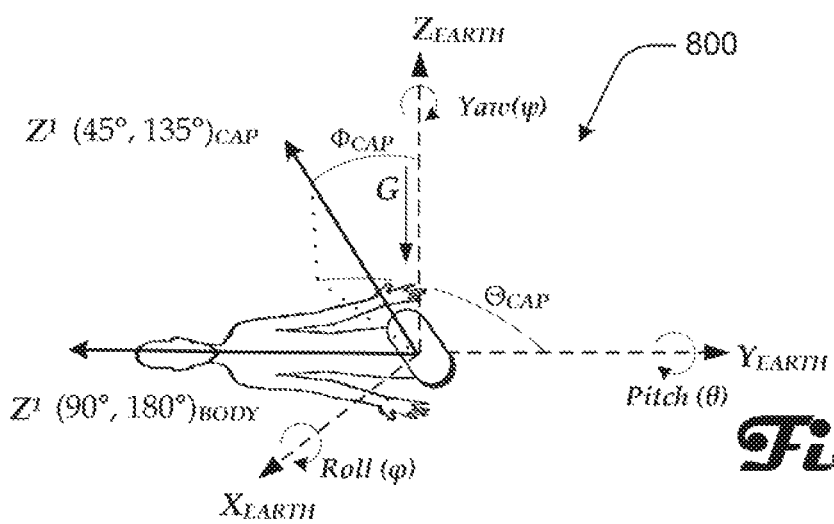
Figure 11:
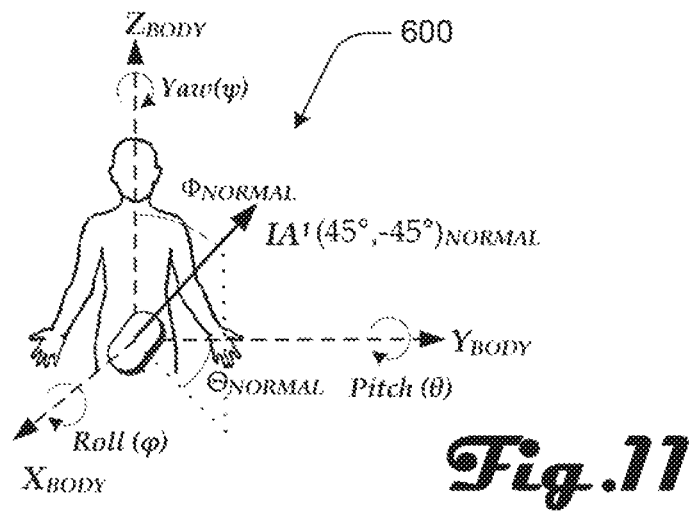

Given that the $Z^N_{CAP}$ CAP and $Z^N_{BODY}$ orientations may be both continuously and independently changing relative to each other over time, the orientation of $Z^N_{CAP}$ relative to the body coordinate system 600 may be calculated by synchronizing or calibrating the frame of reference of the external unit 115 and the frame of reference of the imaging capsule 110 (FIGS. 1-5) relative to each other, relative to the terrestrial coordinate system 800, at $Z^0_{CAP}$ and $Z^0_{BODY}$ and then tracking the orientations of the imaging capsule 110 and external unit 115 (which is assumed to represent the body frame of reference) over time as images are captured by the imaging capsule 110. As depicted in FIG. 9, the frame of reference of the external unit 115 can be assumed to have the same origin as $X_{EARTH}$ $Y_{EARTH}$ $Z_{EARTH}$ coordinate system 800. Also, the frame of reference of the imaging capsule 110 may not be aligned with the frame of reference of the external unit 115; however, the frame of reference of the imaging capsule 110 may also be assumed to have the same origin as the $X_{EARTH}$ $Y_{EARTH}$ $Z_{EARTH}$ coordinate system 800 as depicted in FIGS. 10 and 11. Therefore, the external unit 115 frame of reference and imaging capsule 110 frame of reference can be translated into the $X_{EARTH}$ $Y_{EARTH}$ $Z_{EARTH}$ coordinate system 800 so that the orientations $Z^N_{CAP}$ and $Z^N_{BODY}$ are within a common frame of reference and these orientations may be assumed to be relative to the origin of the $X_{EARTH}$ $Y_{EARTH}$ $Z_{EARTH}$ coordinate system 800, regardless of the position of the external unit 115 (i.e., the subject 100) or imaging capsule 110, relative to each other.

For example, a doctor may initially synchronize or calibrate the external unit 115 and imaging capsule 110 by having the subject 100 stand while wearing the external unit coincident to or parallel with the gravitational force of earth $\vec{G}$ and $Z_{BODY}$, while the doctor holds the imaging capsule parallel with the gravitational force of earth (e.g., away from the ground), as depicted in FIG. 9. The external unit 115 and imaging capsule 110 may be calibrated or synchronized, e.g., by pressing a button on the external unit, or via the computer 510 (FIG. 5). The orientations of the external unit 115 and imaging capsule 110 may thereafter be tracked in relation to each other over time as the subject 100 swallows the imaging capsule and as the imaging capsule travels through the subject's GI tract 140.

For example, presuming that the external unit 115 and imaging capsule 110 are initially synchronized or calibrated having the orientations depicted in FIG. 9 (i.e., $Z^O{}_{CAP}=(0,0)$ and $Z^O{}_{BODY}=(0,0)$), the external unit 115 and imaging capsule 110 will be assumed to both change orientation relative to the earth coordinate system 800 from these respective initial orientations. Any change in orientations of the external unit 115 and imaging capsule 110 may be tracked relative to these initial orientations based on changes in orientation detected by the respective gyroscopes 430, 530 (FIGS. 4 and 5). Roll, pitch and yaw $\varphi$, $\theta$, $\psi$ indicated by the gyroscopes 430, 530 may be converted into spherical coordinates or other desirable orientation indications by known methods. (Note the lower-case symbols $\varphi$, $\theta$, $\psi$ of roll, pitch and yaw as opposed to the upper-case symbols $\Theta$ and $\Phi$, in spherical coordinates).

Accordingly, as the subject 100 and external unit 115 change orientation, and as the imaging capsule 110 changes orientation within the subject 100 while capturing images, the orientation of the image axis 145 may be determined relative to the subject coordinate system 600 (FIG. 6) but independent of the orientation of the external unit 115 (i.e., the subject 100) within the terrestrial frame of reference 800.

For example, assume that the external unit 115 and imaging capsule 110 are initially synchronized or calibrated having the initial orientations depicted in FIG. 9, (i.e., $Z^O{}_{CAP}=(0,0)$ and $Z^O{}_{BODY}=(0,0)$). Then assume that the subject 100 and imaging capsule assume the orientations depicted in FIG. 10, wherein the subject reclines such that $Z^1{}_{BODY}=(90°, 180°)$ and that $Z^1{}_{CAP}=(45°, 135°)$. Further assume that the capsule gyroscope 430 reports a roll, pitch and yaw of $R^1$ ($-45°$ $45°$, $-90°$)$_{CAP}$ and that body gyroscope 530 reports a roll, pitch and yaw of $R^1$ ($-90°$, 0, $-90°$)$_{BODY}$.

To determine the normalized rotation ($R^N{}_{NORMAL}$) and normalized orientation ($O^N{}_{NORMAL}$) of the image axis 145 (i.e., the orientation of the image axis relative to the body coordinate system 600 frame of reference), one may use the following equation: $R^1$ ($\Phi$, $\Theta$, $\Psi$)$_{CAP}$ – $R^1$($\Phi$, $\Theta$, $\Psi$)$_{BODY}$=$R^1$ ($\varphi$, $\theta$, $\psi$)$_{NORMAL}$ (i.e., $R^1\varphi_{CAP}$–$R^1\varphi_{BODY}$=$R^1$ $\varphi_{NORMAL}$; $R^1\theta_{CAP}$–$R^1\theta_{BODY}$=$R^1\theta_{NORMAL}$; $R^1\psi_{CAP}$–$R^1\psi_{BODY}$=$R^1\psi_{NORMAL}$). Returning to the example above, ($\varphi$, $\theta$, $\psi$)$_{NORMAL}$ may be calculated as follows: $R^1$($-45°$, $45°$, $-90°$)$_{CAP}$–$R^1$($-90°$, $0.0°$, $90°$)$_{BODY}$=$R^1$($45°$, $45°$, $-0°$)$_{NORMAL}$. As depicted in FIG. 11, this corresponds to a normalized orientation $O^1{}_{NORMAL}$ of $O^1$($45°$, $45°$)$_{NORMAL}$.

Images captured by the imaging capsule 110 may be associated with a given time so that the image orientation (i.e., the orientation of the image axis 145) may be determined at a number of discrete times. For example, $I^1$ (image 1) may be associated with $Z^1{}_{CAP}$ and $Z^1{}_{BODY}$ and a determination of $0^1{}_{NORMAL}$ would therefore be an indication of the normalized orientation of $I^1$ relative to the body of the subject 100 and the body coordinate system 600 frame of reference (FIGS. 6 and 11) at $T^1$. Additionally, $I^1$ (image 1) may be associated with $R^1{}_{CAP}$ and $R^1{}_{BODY}$ and a determination $R^1{}_{NORMAL}$ may be the normalized rotation of $I^1$ relative to the body of the subject 100 and the body coordinate system 600 frame of reference.

Images and corresponding data may be captured at various suitable intervals. For example, images and corresponding data may be captured every second, tenth of a second, or five images every tenth of a second, with one second between a set of such five images.

From the foregoing it will be appreciated that, although specific embodiments have been described herein for purposes of illustration, various modifications may be made without deviating from the spirit and scope of the disclosure.

Furthermore, where an alternative is disclosed for a particular embodiment, this alternative may also apply to other embodiments even if not specifically stated.

What is claimed is:

1. A system comprising:
    an external unit comprising a first housing, a first gyroscope disposed in the first housing, the external unit configured to be worn by a moveable subject having a body frame of reference while the moveable subject is undergoing motion, the first gyroscope configured to obtain a first measurement by detecting a first yaw, a first pitch, and a first roll relative to an initial frame of reference that is fixed relative to a terrestrial frame of reference;
    an imaging capsule configured to capture images and transmit the images to the external unit when the body frame of reference is moving relative to the terrestrial frame of reference, the imaging capsule comprising
        a second housing with a focal axis extending from a transparent portion of the second housing,
        a pixel array to capture the images through the transparent portion being disposed in the second housing,
        a wireless transmitter to transmit images captured by the pixel array disposed in the second housing,
        a second gyroscope disposed in the second housing, the second gyroscope being configured to obtain a second measurement by detecting, for each image transmitted by the imaging capsule, a second yaw, a second pitch, and a second roll relative to the initial frame of reference, the wireless transmitter in the imaging capsule being configured to transmit the captured images and the second yaw, the second pitch, and the second roll to the external unit comprising the first gyroscope;
    a processor;
    a memory storing a program, the program causing the processor to determine image-axis orientation associated with each image transmitted by the imaging capsule based upon the first and the second measurements from the first and the second gyroscopes, the program comprising further instructions that cause the processor to
        receive the first yaw, the first pitch, the first roll, the second yaw, the second pitch, and the second roll for each image transmitted by the imaging capsule, and
        compute a difference between the first yaw and the second yaw, the first pitch and the second pitch, and the first roll and the second roll, the differences indicating the focal axis relative to the moveable subject for each image captured by the imaging capsule; and
        initialize the first gyroscope and the second gyroscope to the initial frame of reference upon determining that the imaging capsule and the external unit are aligned to the terrestrial frame of reference.

2. The system of claim 1, wherein the external unit further comprises a wireless receiver configured to receive the first yaw, the first pitch, and the first roll from the imaging capsule and send the received first yaw, first pitch, and first roll to the processor.

3. The system of claim 2, wherein the imaging capsule is configured to be located within a gastrointestinal tract of the moveable subject.

4. The system of claim 2, wherein the first gyroscope and the wireless receiver are disposed on a single integrated circuit die.

5. The system of claim 1, further comprising a harness coupled to the external unit and configured to maintain an alignment of the first gyroscope with the moveable subject.

6. The system of claim 1, further comprising a power source coupled to the processor and coupled to the first gyroscope.

7. The system of claim 1, further comprising a power source coupled to the second gyroscope.

8. The system of claim 1, further comprising a memory configured to store the difference between the first yaw and the second yaw, the first pitch and the second pitch, and the first roll and the second roll.

9. A wearable device comprising:
a first gyroscope configured to obtain a first measurement by detecting a first yaw, a first pitch, and a first roll relative to an initial frame of reference that is fixed relative to a terrestrial frame of reference, the wearable device being configured to be temporarily attached to a moveable subject in a fixed position relative to the moveable subject when the moveable subject is undergoing motion;
a wireless receiver configured to
receive, when the wearable device is undergoing motion relative to the terrestrial frame of reference, images captured by an imaging capsule within a moveable body, and second measurements comprising a second yaw, a second pitch, and a second roll relative to the initial frame of reference detected at a second gyroscope located within the imaging capsule, the imaging capsule comprising a housing with a focal axis extending from a transparent portion of the housing, a pixel array disposed in the housing to capture images through the transparent portion;
a power source; and
a processor;
a memory storing a program, the program causing the processor to determine image-axis orientation associated with each of the captured images based upon the first and the second measurements from the first and the second gyroscopes, the program comprising further instructions that cause the processor to
receive the first yaw, the first pitch, the first roll, the second yaw, the second pitch, and the second roll, and
compute a difference between the first yaw and the second yaw, the first pitch and the second pitch, and the first roll and the second roll, the differences indicating the focal axis relative to the moveable subject for each image captured by the imaging capsule; and
initialize the first gyroscope to the initial frame of reference upon determining that the imaging capsule and the wearable device are aligned to the terrestrial frame of reference, wherein the wearable device is configured to be worn by a moveable subject during motion.

10. The wearable device of claim 9, wherein the imaging capsule is configured to be located within a gastrointestinal tract of the moveable subject.

11. The wearable device of claim 9, wherein the wireless receiver is configured to send the received first yaw, first pitch, and first roll to the processor.

12. The wearable device of claim 9, wherein the first gyroscope and the wireless receiver are disposed on a single integrated circuit die.

13. The wearable device of claim 9, further comprising a harness coupled to the wearable device and configured to maintain an alignment of the first gyroscope with the moveable subject.

14. The wearable device of claim 9, wherein the power source is coupled to the processor and to the first gyroscope.

15. The wearable device of claim 9, further comprising a memory configured to store the difference between the first yaw and the second yaw, the first pitch and the second pitch, and the first roll and the second roll.

16. A wearable device comprising:
a first gyroscope configured to obtain a first measurement by detecting a first yaw, a first pitch, and a first roll relative to an initial frame of reference that is fixed relative to a terrestrial frame of reference, the wearable device being configured to be temporarily remain attached to a moveable subject in a fixed position relative to the moveable subject during motion of the moveable subject;
a power source;
a wireless device configured to
receive, when the wearable device is undergoing motion relative to the terrestrial frame of reference, images captured by an imaging capsule within a moveable body, and second measurements comprising a second yaw, a second pitch, and a second roll relative to the initial frame of reference detected at a second gyroscope located within the imaging capsule, the imaging capsule comprising a housing with a focal axis extending from a transparent portion of the housing, a pixel array disposed in the housing to capture images through the transparent portion,
send the first yaw, the first pitch, the first roll, the second yaw, the second pitch, and the second roll to a processor, wherein a program stored in a non-transitory memory when executed causes the processor to determine image-axis orientation associated with each of the captured images based upon the first and the second measurements from the first and the second gyroscopes, the program comprising further instructions that cause the processor to
receive the first yaw, the first pitch, the first roll, the second yaw, the second pitch, and the second roll, and
compute a difference between the first yaw and the second yaw, the first pitch and the second pitch, and the first roll and the second roll, the differences indicating the focal axis relative to the moveable subject for each image captured by the imaging capsule, and
initialize the first gyroscope to the initial frame of reference upon determining that the imaging capsule and the wearable device are aligned to the terrestrial frame of reference; and
a memory configured to store the captured images and the first yaw, the first pitch, the first roll, the second yaw, the second pitch, and the second roll.

17. The wearable device of claim 16, wherein the imaging capsule is configured to be located within a gastrointestinal tract of the moveable subject.

18. The wearable device of claim 16, wherein the first gyroscope and the wireless device are disposed on a single integrated circuit die.

19. The wearable device of claim 16, further comprising a harness coupled to the wearable device and configured to maintain an alignment of the first gyroscope with the moveable subject.

20. The wearable device of claim 16, wherein the power source is coupled to the processor and to the first gyroscope.

21. The system of claim 1, wherein the external unit further comprises a wireless device configured to receive the first yaw, the first pitch, and the first roll from the imaging capsule and send the received first yaw, first pitch, and first roll to the processor, wherein the imaging capsule is configured to be located within the moveable subject, wherein after initializing the first gyroscope and the second gyroscope to the initial frame of reference, the imaging capsule is configure to capture images through the pixel array when the imaging capsule traverses within the moveable subject and when the external unit is attached to the moveable subject so that image data is sent from the wireless transmitter to the wireless device and image-axis orientations associated with the image data are determined based upon the first and second gyroscopes.

22. The system of claim 21, further comprising:
- a first power source disposed in the second housing of the imaging capsule, the first power source being coupled to the processor and to the first gyroscope;
- a light source disposed in the second housing of the imaging capsule, the light source configured to provide illumination to the pixel array for capturing an image while in the movable subject; and
- a second power source coupled to the second gyroscope.

23. The system of claim 22, wherein the light source is configured to provide continuous illumination.

24. The system of claim 22, wherein the light source is configured to provide flash illumination.

25. The system of claim 22, wherein the first gyroscope and the wireless device are disposed on a single integrated circuit die.

26. The wearable device of claim 9, wherein the wireless receiver is configured to send the received first yaw, first pitch, and first roll to the processor, wherein the imaging capsule is configured to be located within a gastrointestinal tract (GI) of the moveable subject, wherein after initializing the first gyroscope and the second gyroscope to the initial frame of reference, the imaging capsule is configure to capture images when the imaging capsule traverses the GI track of the moveable subject and when the wearable device is attached to the moveable subject so that image data is received at the wireless receiver and image-axis orientations associated with the image data are determined based upon the first and second gyroscopes.

* * * * *